(12) United States Patent
Tsuji et al.

(10) Patent No.: US 7,655,130 B2
(45) Date of Patent: Feb. 2, 2010

(54) **GLUCOSE DEHYDROGENASE FROM *ASPERGILLUS ORYZAE***

(75) Inventors: Yuji Tsuji, Tsuruga (JP); Masao Kitabayashi, Tsuruga (JP); Takahide Kishimoto, Tsuruga (JP); Yoshiaki Nishiya, Tsuruga (JP)

(73) Assignee: Toyo Boseki Kabushiki Kaisha, Osaka-shi (JP)

( * ) Notice: Subject to any disclaimer, the term of this patent is extended or adjusted under 35 U.S.C. 154(b) by 0 days.

(21) Appl. No.: 12/467,407

(22) Filed: May 18, 2009

(65) Prior Publication Data

US 2009/0259024 A1      Oct. 15, 2009

Related U.S. Application Data

(63) Continuation of application No. 11/692,678, filed on Mar. 28, 2007, now Pat. No. 7,553,649.

(60) Provisional application No. 60/788,252, filed on Mar. 31, 2006, provisional application No. 60/868,276, filed on Dec. 1, 2006.

(51) Int. Cl.
*G01N 27/26* (2006.01)
*C12N 9/04* (2006.01)

(52) U.S. Cl. .................... 205/777.5; 435/190

(58) Field of Classification Search .............. 205/777.5; 435/190
See application file for complete search history.

(56) References Cited

U.S. PATENT DOCUMENTS

| 4,877,733 | A | 10/1989 | Takahashi et al. |
| 5,723,284 | A | 3/1998 | Ye |
| 7,371,836 | B2 | 5/2008 | Desnoyers et al. |

| 2004/0023330 | A1 | 2/2004 | Sode |
| 2006/0063217 | A1 | 3/2006 | Omura et al. |
| 2007/0105174 | A1 | 5/2007 | Aiba et al. |
| 2008/0003628 | A1 | 1/2008 | Kitabayashi et al. |
| 2008/0014611 | A1 | 1/2008 | Kitabayashi et al. |
| 2008/0014612 | A1 | 1/2008 | Tsuji et al. |
| 2008/0020426 | A1 | 1/2008 | Aiba et al. |
| 2008/0090278 | A1 | 4/2008 | Kitabayashi et al. |

FOREIGN PATENT DOCUMENTS

| EP | 1 584 675 A1 | 10/2005 |
| EP | 1 862 543 A1 | 12/2007 |
| JP | 10-010130 A | 1/1998 |
| WO | WO 02/36779 A1 | 5/2002 |
| WO | WO 03/012071 A2 | 2/2003 |
| WO | WO 2004-058958 A1 | 7/2004 |
| WO | WO 2006-101239 A1 | 9/2006 |

OTHER PUBLICATIONS

Bak et al., *Biochimica et Biophysica Acta*, 139: 265-276 (1967).
Bak, *Biochimica et Biophysica Acta*, 139: 277-293 (1967).
Bak, *Biochimica et Biophysica Acta*, 146: 317-327 (1967).
Bak et al., *Biochimica et Biophysica Acta*, 146: 328-335 (1967).
Belenky et al., *Antibiotiki*, 18: 602-603 (Jul. 1964), Russian.
Elzainy et al., *Ann. Microbiol. Enzimol.*, 43: 169-179 (1993).
Machida et al., *Nature*, 438: 1157-1161 (2005).
Müller, *Arch. Microbiol.*, 144: 151-157 (1986).
Scognamiglio et al., *Journal of Fluorescence*, 14(5): 491-498 (Sep. 2004).
Database UNIPROT, Entry Name "Q2USF2_ASPOR," Accession No. Q2USF2 (Jan. 24, 2006).

*Primary Examiner*—Maryam Monshipouri
(74) *Attorney, Agent, or Firm*—Leydig, Voit & Mayer, Ltd.

(57) ABSTRACT

The present invention effectively produces glucose dehydrogenase derived from *Aspergillus oryzae*, and provides more practical glucose dehydrogenase. The invention makes it possible to efficiently produce glucose dehydrogenase and to obtain glucose dehydrogenase in more practical manner by using a glucose dehydrogenase gene isolated from *Aspergillus oryzae*.

4 Claims, No Drawings

GLUCOSE DEHYDROGENASE FROM *ASPERGILLUS ORYZAE*

CROSS-REFERENCE TO RELATED APPLICATIONS

This patent application is a continuation of U.S. patent application Ser. No. 11/692,678, filed Mar. 28, 2007, now U.S. Pat. No. 7,553,649 which claims priority to U.S. Provisional Application Nos. 60/788,252, filed Mar. 31, 2006, and 60/868,276, filed Dec. 1, 2006.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 21,447 bytes ASCII (Text) file named "704903SequenceListing.txt" created May 15, 2009.

TECHNICAL FIELD

The present invention relates to a gene encoding glucose dehydrogenase derived from *Aspergillus oryzae* and a method for producing the glucose dehydrogenase by gene recombination.

BACKGROUND ART

Self-monitoring of blood glucose is important for a patient with diabetes to figure out a usual blood glucose level in the patient and apply it to treatment. An enzyme taking glucose as a substrate is utilized for a sensor used for the self-monitoring of blood glucose. An example of such an enzyme includes, for example, glucose oxidase (EC. 1.1.3.4). Glucose oxidase is advantageous in that it has high specificity for glucose and is excellent in thermal stability, and thus has been used as the enzyme for a blood glucose sensor from a long time ago. Its first publication goes back 40 years ago. In the blood glucose sensor using glucose oxidase, the measurement is performed by transferring electrons produced in a process of oxidizing glucose to convert into D-glucono-δ-lactone to an electrode via a mediator. However, glucose oxidase easily transfers protons produced in the reaction to oxygen, and thus dissolved oxygen affects the measured value, which has been problematic.

In order to avoid such a problem, for example, NAD(P)-dependent glucose dehydrogenase (EC. 1.1.1.47) or pyrroloquinoline quinone-dependent glucose dehydrogenase (EC. 1.1.5.2; former EC. 1.1.99.17) is used as the enzyme for the blood glucose sensor. They dominates in that they are not affected by dissolved oxygen, but the former NAD(P)-dependent glucose dehydrogenase has the poor stability and requires the addition of the coenzyme. Meanwhile, the latter pyrrolo-quinoline quinone-dependent glucose dehydrogenase is inferior in substrate specificity, reacts with other sugars such as maltose and lactose and thus correctness of the measured value is impaired.

In Non-patent documents 1 to 4, glucose dehydrogenase derived from *Aspergillus oryzae* has been reported, but no glucose dehydrogenase gene has been reported. In Non-patent documents 1 to 4, it has not been described to produce the glucose dehydrogenase derived from *Aspergillus oryzae* by gene recombination.

Non-patent literature 1: Biochim. Biophys. Acta., 1967 Jul. 11; 139(2):265-76

Non-patent literature 2: Biochim. Biophys. Acta., 1967 Jul. 11; 139(2):277-93

Non-patent literature 3: Biochim Biophys Acta. 146(2):317-27

Non-patent literature 4: Biochim Biophys Acta. 146(2):328-35

In Patent document 1, flavin-binding type glucose dehydrogenase derived from genus *Aspergillus* has been disclosed. This enzyme dominates in that this is excellent in substrate specificity and is not affected by the dissolved oxygen. For the thermal stability, it has been described that a residual activity ratio after being treated at 50° C. for 15 minutes is about 89% and this enzyme is excellent in thermal stability (hereinafter also described as heat resistance). In Patent document 2, a gene sequence and an amino acid sequence of that enzyme have been reported.

Patent document 1: WO2004/058958

Patent document 2: WO2006/101239

Recently, a complete genome sequence of *Aspergillus oryzae* has been determined. However, there is no available information what part of the sequence encodes glucose dehydrogenase.

DISCLOSURE OF THE INVENTION

It is an object of the present invention to provide a method for efficiently producing the practically more advantageous enzyme for the blood glucose sensor. More specifically, it is the object to establish the method for stably producing glucose dehydrogenase derived from *Aspergillus oryzae* on a large scale by specifying, acquiring and utilizing a gene encoding the glucose dehydrogenase.

For accomplishing the above objects, the present inventors presumed and acquired a glucose dehydrogenase gene derived from *Aspergillus oryzae* by utilizing database of National Center for Biotechnology Information (NCBI) and found that glucose dehydrogenase derived from *Aspergillus oryzae* could be acquired from *Escherichia coli* using the gene.

According to the present invention, by utilizing the glucose dehydrogenase gene isolated from *Aspergillus oryzae*, it becomes possible to efficiently produce glucose dehydrogenase and acquire more practical glucose dehydrogenase.

Thus, the present invention comprises the following

[1] A gene composed of the following DNA (a), (b), (c) or (d):

(a) DNA composed of a base sequence described in SEQ ID NO:5;

(b) DNA composed of a base sequence described in SEQ ID NO:8, comprising a base sequence described in SEQ ID NO:5 and intron;

(c) DNA which hybridizes with DNA composed of a base sequence complementary to DNA (a) under a stringent condition and encodes a protein having a glucose dehydrogenase activity; or (d) DNA which hybridizes with DNA composed of a base sequence complementary to DNA (b) under the stringent condition and comprises a region encoding the protein having the glucose dehydrogenase activity.

[2] A gene encoding the following protein (a) or (b):

(a) a protein composed of an amino acid sequence described in SEQ ID NO:4; or (b) a protein composed of an amino acid sequence having one or more amino acid deletions, substitutions or additions (insertions) in the amino acid sequence described in SEQ ID NO:4, and having a glucose dehydrogenase activity.

[3] A recombinant vector comprising the gene according to any of [1] or [2].

[4] A transformant transformed with the recombinant vector according to [3].

[5] The transformant according to [4] wherein a host is *Escherichia coli*.

[6] A method for producing a protein having a glucose dehydrogenase activity, characterized in that the transformant according to [4] or [5] is cultured in a nutrient medium and the protein having the glucose dehydrogenase activity is collected.

According to the present invention, it has become possible to efficiently produce glucose dehydrogenase. It has become easy to perform molecular biological improvement in order to obtain more practical glucose dehydrogenase.

BEST MODES FOR CARRYING OUT THE INVENTION

In order to accomplish the above objects, the present inventors found a gene DNA presumed to encode glucose dehydrogenase (hereinafter sometimes abbreviated as ATGDH) by utilizing the NCBI database.

A DNA (gene) composed of the base sequence described in SEQ ID NO:1 is a genomic gene sequence comprising a DNA (gene) encoding glucose dehydrogenase derived from *Aspergillus oryzae* RIB40 strain, predicted from the NCBI database, where no intron has been eliminated.

A DNA composed of the base sequence described in SEQ ID NO:2 is obtained by removing the intron from the sequence of SEQ ID NO: 1

The gene encoding a protein composed of an amino acid sequence described in SEQ ID NO:3 indicates the entire sequence of a glucose dehydrogenase gene predicted from the NCBI database.

The present inventors predicted from Non-patent literatures 1 to 4 and the NCBI database that the DNA (gene) encoding the protein having the glucose dehydrogenase activity derived from *Aspergillus oryzae* could be easily identified.

And further, they thought that it was also easy that a recombinant vector containing the gene was made, a transformant was made and a protein encoded by the gene expressed by the transformant was purified.

Although the amino acid sequence and the base sequence encoding flavin-binding glucose dehydrogenase derived from *Aspergillus oryzae* were not specified in the NCBI database, specifically, with reference to the methods described in Non-patent literatures 1 to 4 and publicly known technologies, the present inventors tried to culture *Aspergillus oryzae*, purify glucose dehydrogenase (GDH) from its culture supernatant using various chromatography methods, make a probe by analyzing its terminal amino acid sequence and isolate the gene encoding the glucose dehydrogenase.

Likewise, the present inventors tried to isolate the gene encoding glucose dehydrogenase by independently obtaining a microorganism belonging to genus *Aspergillus terreus*.

Although the present inventors studied variously, it was found that it was difficult to obtain a GDH preparation with high purity whose band could be clearly identified on SDS-PAGE from the culture supernatant of *Aspergillus oryzae* TI strain by ordinary purification methods using salting out and chromatography methods. It was speculated that sugar chains supposed to be bound to the enzyme protein was one of causes to make the purification and identification difficult. Therefore, they determined that they had no choice but to give up the cloning utilizing the partial amino acid sequence, which was one of standard methods for acquiring the gene.

Thus, with many trials and errors, it was extremely difficult to acquire the gene, but as a result of an extensive study, the present inventors isolated the gene encoding the flavin-binding glucose dehydrogenase derived from *Aspergillus oryzae* and completed the present invention.

Its detail will be described later in Examples 1 to 3.

One embodiment of the present invention is a method for producing a protein having a glucose dehydrogenase activity characterized by culturing a transformant transformed with a recombinant vector comprising a gene composed of any DNA of the following (a), (b), (c) and (d) or a gene encoding a protein of the following (e) or (f) in a nutrient medium and collecting the protein having the glucose dehydrogenase activity.

(a) DNA (gene) composed of a base sequence described in SEQ ID NO:5 indicates the entire sequence of DNA (gene) encoding the protein having the glucose dehydrogenase activity derived from *Aspergillus oryzae* TI strain described later, identified by the present inventors.

(c) DNA (gene) which hybridizes DNA composed of the base sequence complementary to DNA composed of the base sequence described in SEQ ID NO:5 under the stringent condition and encodes the protein having the glucose dehydrogenase activity is also included in the present invention.

(b) DNA (gene) composed of the base sequence described in SEQ ID NO:8 is a genomic gene sequence comprising DNA (gene) encoding the protein having the glucose dehydrogenase activity derived from *Aspergillus oryzae* TI strain described later, where no intron has been eliminated.

(d) DNA which hybridizes DNA composed of the base sequence complementary to DNA composed of the base sequence described in SEQ ID NO:8 under the stringent condition and comprises a region encoding the glucose dehydrogenase activity is also included in the present invention.

(e) The gene encoding the protein composed of the amino acid sequence described in SEQ ID NO:4 indicates the entire sequence of DNA (gene) encoding the protein having the glucose dehydrogenase activity derived from *Aspergillus oryzae* TI strain described later.

(f) DNA (gene) encoding a protein composed of the amino acid sequence having one or more amino acid deletions, substitutions or additions (insertions) in the amino acid sequence described in SEQ ID NO:4 and having the glucose dehydrogenase activity is also included in the present invention.

Those skilled in the art can easily select the stringent condition by changing the temperature in the hybridization reaction and the washing and salt concentrations in a hybridization reaction solution and a washing solution. Specifically, the condition where the hybridization is performed in 6×SSC (0.9 M NaCl, 0.09 M trisodium citrate) or 6×SSPE (3M NaCl, 0.2 M NaH$_2$PO$_4$, 20 mM EDTA 2Na, pH 7.4) at 42° C. and further the washing is performed with 0.5×SSC at 42° C. is included as one example of the stringent condition of the present invention, but the stringent condition is not limited thereto. Preferably, the condition where the hybridization is performed in 50% formamide, 6×SSC (0.9 M NaCl, 0.09 M trisodium citrate) or 6×SSPE (3 M NaCl, 0.2 M NaH$_2$PO$_4$, 20 mM EDTA 2Na, pH 7.4) at 42° C. and further the washing is performed with 0.1×SSC at 42° C. is included.

The DNA (gene) of the present invention can include those in which codon usage has been changed to enhance the expression of the GDH.

For example, the above GDH gene derived from *Aspergillus oryzae* is inserted into an expression vector (many vectors such as plasmids are known in the art), and an appropriate host (many hosts such as *Escherichia coli* are known in the art) is transformed with the expression vector. A water soluble fraction containing GDH can be yielded by culturing the resulting transformant, collecting microbial cells from the medium by centrifugation, disrupting the microbial cells by a mechanical method or an enzymatic method, e.g., using lysozyme and if necessary adding a chelating agent such as EDTA and a surfactant to solubilize. Alternatively, by the use of an appropriate host-vector system, it is possible to secret the expressed GDH directly in the medium.

A GDH containing solution obtained as the above could be precipitated by concentration under reduced pressure, membrane concentration, salting out treatment using ammonium sulfate or sodium sulfate or fractional precipitation using a hydrophilic organic solvent such as methanol, ethanol or acetone. The treatment with heat and isoelectric focusing treatment are also effective purification procedures. The purified GDH can also be yielded by performing gel filtration using an absorbing agent or a gel filtration agent, absorption chromatography, ion exchange chromatography and affinity chromatography. It is preferable that the purified enzyme preparation is purified to an extent that the enzyme is detected as a single band on electrophoresis (SDS-PAGE).

These can be carried forward in accordance with the following references.

(a) *Tanpakushitsu Jikken Protocol* Vol. 1, Functional Analysis Vol. 2, Structural Analysis (Shujunsha) edited by Yoshifumi Nishimura and Shigeo Ohno.

(b) *Revised Tanpakushitsu Jikken Note*, Extraction and Separation/Purification (Yodosha) edited by Masato Okada and Kaori Miyazaki.

(c) *Tanpakushitsu Jikken no Susumekata* edited by Masato Okada and Kaori Miyazaki.

Alternatively, the above procedures can also be carried forward by methods exemplified below.

The produced DNA having genetic information of the protein is transferred into the host microorganism by ligating to the vector.

As the vector, those constructed for gene recombination from a phage or a plasmid capable of independently replicating in the host microorganism are suitable. As the phage, for example, Lambda gt10 and Lambda gt11 is exemplified when *Escherichia coli* is used as the host microorganism. As the plasmid, for example, pBR322, pUC19, pKK223-3 and pBluescript are exemplified when *Escherichia coli* is used as the host microorganism. Among them, those such as pbluescript carrying the promoter capable of being recognized in *Escherichia coli* upstream of a cloning site are preferable.

The appropriate host microorganism is not particularly limited as long as the recombinant vector is stable therein and can independently replicate and a trait of a foreign gene can be expressed. For *Escherichia coli, Escherichia coli* W3110, *Escherichia coli* C600, *Escherichia coli* HB101, *Escherichia coli* JW109 and *Escherichia coli* DH5α can be used.

As the method for transferring the recombinant vector into the host microorganism, for example, when the host microorganism belongs to genus *Escherichia*, the method of transferring recombinant DNA in the presence of Ca ions can be employed, and further, an electroporation method may be used. Furthermore, commercially available competent cells (e.g., Competent High DH5α supplied from Toyobo Co., Ltd.) may be used. When the yeast is used as the host, a lithium method or an electroporation method is used. When filamentous fungus is used, a protoplast method is used.

In the present invention, the method for yielding the gene encoding GDH includes the following methods. The predicted GDH gene can be found by using the information for a genomic sequence of *Aspergillus oryzae*. Then, mRNA is prepared from the microbial cells of *Aspergillus oryzae* and cDNA is synthesized. The GLD gene is amplified by PCR using the cDNA obtained in this way as the template, and the recombinant vector is constructed by binding and closing this gene and the vector at blunt ends or sticky ends of both DNA with DNA ligase. The recombinant vector is transferred into the host microorganism in which the vector can replicate, and subsequently, the recombinant microorganism containing the gene encoding GDH is obtained by utilizing a marker of the vector.

GDH in a large amount can be stably produced by culturing the microorganism which is the transformant yielded as the above in the nutrient medium. The transformant could be selected by searching the microorganism which has expressed the marker of the vector and the GDH activity simultaneously. For example, the microorganism which grows in a selection medium based on a drug resistant marker and generates GDH could be selected.

The base sequence of the GDH gene was decoded by a dideoxy method described in Science 214:1205, 1981. The amino acid sequence of GDH was deduced from the base sequence determined as the above.

As in the above, the once selected GDH gene in the recombinant vector can be easily transferred into another recombinant vector which can replicate in another microorganism by collecting the DNA which is the GDH gene from the recombinant vector carrying the GDH gene by restriction enzymes and PCR method and binding the DNA to another vector fragment. For the transformation of another microorganism with these vectors, the competent cell method by treating with calcium, the electroporation method and the protoplast method can be used.

The GDH gene of the present invention may be those having the DNA sequence so that a part of amino acid residues is deleted or substituted in the amino acid sequence after translation of the gene or so that other amino acid residues are added or substituted, as long as the protein encoded by the GDH gene has the glucose dehydrogenase activity.

As the method for modifying the gene encoding the wild type GDH, the typically performed technique to modify the genetic information is used. That is, DNA having the genetic information of the modified protein is made by converting the specific base in DNA having the genetic information of the protein or inserting or deleting the specific base. The specific methods for converting the base in the DNA include the use of commercially available kits (Transformer Mutagenesis Kit supplied from Clonetech; EXQIII/Mung Bean Deletion Kit supplied from Stratagene; QuickChange Site Directed Mutagenesis Kit supplied from Stratagene), or utilization of polymerase chain reaction (PCR) method.

For the culture of the host microorganism which is the transformant, a culture condition could be selected in consideration of nutritional physiological natures of the host. It is advantageous that the transformant is cultured in liquid culture in many cases and industrially ventilation stirring culture is performed. But, considering the productivity, it is more advantageous in some cases that the filamentous fungus is used as the host and a solid culture is employed.

As nutrient sources of the medium, those typically used for the culture of the microorganism can be widely used. Carbon sources may be carbon compounds capable of being assimilated. For example, glucose, sucrose, lactose, maltose, lactose, molasses and pyruvic acid are used. Nitrogen sources may be usable nitrogen compounds. For example, peptone, meat extracts, yeast extracts, casein hydrolyzed products, and bean cake extracted with alkali are used. In addition, phosphate salts, carbonate salts, sulfate salts, salts of magnesium, calcium, potassium, iron, manganese and zinc, particular amino acids and particular vitamins are used if necessary.

A culture temperature can be appropriately changed in the range in which the microorganism grows and produces GDH, and is preferably about 20 to 37° C. A culture time period is somewhat different depending on the condition, the culture could be terminated at an appropriate time period by judging the time to be right to reach the maximum yield of GDH, and the culture time period is typically about 6 to 48 hours.

A pH value in the medium can be appropriately changed in the range in which the microorganism grows and produces the GDH, and is preferably in the range of about pH 6.0 to 9.0.

The culture medium containing the microbial cells which produce GDH can be directly collected and utilized. However, in general, according to standard methods, when the GDH is present in the culture medium, a GDH-containing solution is separated from the microorganism microbial cells by filtration or centrifugation, and subsequently utilized. When GDH is present in the microbial cells, the microbial cells are collected from the culture by filtration or centrifugation, then disrupted by the mechanical method or the enzymatic method using lysozyme and if necessary the chelating agent such as EDTA and the surfactant are added to solubilize, and GDH is separated/collected as an aqueous solution.

The GDH-containing solution obtained as the above could be precipitated by concentration under reduced pressure, membrane concentration, salting out treatment using ammonium sulfate or sodium sulfate or fractional precipitation using the hydrophilic organic solvent such as methanol, ethanol or acetone. The treatment with heat and isoelectric focusing treatment are also effective purification procedures. The purified GDH can also be yielded by subsequently performing gel filtration using the absorbing agent or the gel filtration agent, absorption chromatography, ion exchange chromatography and affinity chromatography.

For example, it is possible to obtain a purified enzyme preparation by separating and purifying by gel filtration using Sephadex gel (supplied from GE Health Care Bioscience), or column chromatography using DEAE Sepharose CL-6B (supplied from GE Health Care Bioscience) or Octyl Sepharose CL-6B (supplied from GE Health Care Bioscience). It is preferable that the purified enzyme preparation is purified to the extent that the enzyme is detected as a single band on electrophoresis (SDS-PAGE).

In the present invention, the glucose dehydrogenase activity is measured under the following condition.

<Reagents>

50 mM PIPES buffer pH 6.5 (including 0.1% Triton X-100)

14 mM 2,6-dichlorophenol-indophenol (DCPIP) solution

1 M D-glucose solution.

A reaction reagent is made by mixing 15.8 mL of the PIPES buffer, 0.2 mL of the DCPIP solution and 4 mL of the D-glucose solution.

<Measurement Condition>

The reaction reagent (2.9 mL) is preliminarily heated at 37° C. for 5 minutes. The GDH solution (0.1 mL) is added and gently mixed, subsequently the change of absorbance at 600 nm is recorded for 5 minutes using a spectrophotometer controlled to 37° C. using water as a control, and the change of absorbance per one minute ($\Delta OD_{TEST}$) is calculated from a linear portion of the record. The solvent in which GDH will be dissolved in place of the blinded GDH solution is added to the reagent mixture, and the change of absorbance ($\Delta OD_{BLANK}$) per one minute is measured. The GDH activity is calculated from these values according to the following formula. One unit (U) in the GDH activity is defined as the amount of the enzyme which reduces 1 µM DCPIP for one minute in the presence of 200 mM D-glucose.

Activity(U/mL)=[−($\Delta OD_{TEST}$−$\Delta OD_{BLANK}$)×3.0× dilution scale]/(16.3×0.1×1.0)

In the above formula, 3.0 represents a liquid amount (mL) of the reaction reagent+the enzyme solution, 16.3 represents a millimolar molecular absorbance coefficient ($cm^2$/µmol) in the condition of measuring the present activity, 0.1 represents the liquid amount of the enzyme solution (mL) and 1.0 represents a light path length (cm) of the cell.

EXAMPLES

The present invention will be more specifically described below by Examples, but the present invention is not limited to the following Examples.

An outline of the procedure to acquire the GDH gene derived from *Aspergillus oryzae* described in Examples shown below is as follows.

In order to acquire the GDH gene derived from *Aspergillus oryzae*, the purification of GDH from the culture supernatant of *Aspergillus oryzae* and *Aspergillus terreus* was tried using salting out, chromatography and the like, but it was difficult to yield GDH with high purity (Example 1 [1])

Therefore, we had no choice but to give up the cloning utilizing the partial amino acid sequence, which was one of standard methods to acquire the gene.

Thus, we searched GDH-producing microorganisms other than the above microorganisms, and as a result of an extensive study, we found that *Penicillium lilacinoechinulatum* NBRC6231 produced GDH, and succeeded to yield the purified enzyme with high purity from the culture medium of this fungal strain (Example 1 [2]).

Subsequently, we succeeded to determine the partial amino acid sequence using the above enzyme, partially acquired the GDH gene derived from *P. lilacinoechinulatum* NBRC6231 by PCR based on the determined amino acid sequence and determined its base sequence (1356 bp) (Example 1 [3] and [4]).

Finally, based on this base sequence, the GDH gene derived from *Aspergillus oryzae* was presumed (Example 1 [5]) from the published database of *Aspergillus oryzae* genome, and it was acquired.

Example 1

Estimation of Glucose Dehydrogenase Gene Derived from *Aspergillus oryzae* (Hereinafter Sometimes Abbreviated as "AOGDH")

[1] Acquisition of GDH Derived from *Aspergillus oryzae*

*Aspergillus oryzae* obtained from soils and stored as dried microbial cells according to standard methods was used. This is referred to as *Aspergillus oryzae* TI strain below.

*Aspergillus oryzae* TI strain was restored by inoculating its dry microbial cells in the potato dextrose agar medium (supplied from Difco) and incubating at 25° C. Fungal threads restored on the plate were collected including the agar, which was then suspended in filtrated sterilized water. In two 10 L jar fermenters 6 L of a production medium (1% malt extract, 1.5% soy bean peptide, 0.1% MgSO$_4$.7H$_2$O, 2% glucose, pH 6.5) was prepared and sterilized by autoclave at 120° C. for 15 minutes. After cooling, the above fungal thread suspension was inoculated, and cultured with ventilation and stirring at 30° C. The culture was stopped 64 hours after the start of the culture, and a filtrate containing the GDH activity was collected by removing the fungal threads by filtration. Low molecular substances were removed from the collected supernatant by ultrafiltration (molecular weight 10,000 cut off). Then, ammonium sulfate was added at 60% saturation to perform ammonium sulfate fractionation. The supernatant containing the GDH activity was collected by centrifugation, adsorbed to the Octyl-Sepharose column, and eluted with ammonium sulfate having the gradient from 60% saturation to 0% to collect fractions having the GDH activity. The resulting GDH solution was applied onto the G-25 Sepharose column to perform the salting out. Ammonium sulfate was added at 60% saturation thereto. The mixture was adsorbed to the Phenyl-Sepharose column and eluted with ammonium sulfate having the gradient from 60% saturation to 0% to collect fractions having the GDH activity. The fraction having the GDH activity was heated at 50° C. for 45 minutes, and then centrifuged to yield the supernatant. The solution obtained from the above steps was made a purified GDH preparation (AOGDH). In the above purification process, 20 mM potassium phosphate buffer (pH 6.5) was used as the buffer. In order to determine the partial amino acid sequence of the AOGDH, the further purification was tried using various procedures such as ion exchange chromatography and gel filtration chromatography, but no purified preparation capable of being subjected to the partial amino acid sequencing could be obtained.

Also, we independently searched and obtained the microorganism belonging to *Aspergillus terreus*, and likewise tried the purification from its culture supernatant by the salting out and the Octyl-Sepharose, but no purified preparation capable of being subjected to the partial amino acid sequencing could be obtained as was the case with *Aspergillus oryzae*. Typically, using the purification methods commonly used, it is possible to obtain the protein preparation with high purity detected as a clear single band on SDS-PAGE. However, the GDH preparation at such a level could not be obtained. It was speculated that one of its causes was the sugar chain thought to be bound to the enzyme protein. Therefore, we had no choice but to give up the cloning utilizing the partial amino acid sequence of the protein, which was one of standard methods to acquire the gene.

[2] Acquisition of GDH Derived from Filamentous Fungus Belonging to Genus *Penicillium*

A purified preparation detected to be nearly uniform on SDS electrophoresis was acquired by using *Penicillium lilacinoechinulatum* NBRC6231 as the GDH producing fungus derived from the filamentous fungus belonging to genus *Penicillium* and performing the culture and the purification according to the same procedure as in the case with the above *Aspergillus oryzae*.

[3] Preparation of cDNA

For *Penicillium lilacinoechinulatum* NBRC6231, according to the above methods, the culture was carried out (but, the culture in the jar fermenter was performed for 24 hours), and the fungal threads were collected by filter paper filtration. The collected fungal threads were immediately frozen in liquid nitrogen, and disrupted using Cool Mill (supplied from Toyobo Co., Ltd.). The total RNA was immediately extracted from disrupted microbial cells using Sepasol RNA I (supplied from Nacalai Tesque) according to the protocol of this kit. mRNA was purified from the resulting total RNA using Origotex-dt3 (supplied from Daiichi Pure Chemicals Co., Ltd.), and RT-PCR with this as the template was performed using ReverTra-Plus™ supplied from Toyobo Co., Ltd. A resulting product was electrophoresed on agarose gel and a portion corresponding to a chain length of 0.5 to 4.0 kb was cut out. cDNA was extracted from a cut out gel fragment using MagExtractor-PCR&Gel Clean Up supplied from Toyobo Co., Ltd. and purified to use as a cDNA sample.

[4] Determination of GDH Gene Partial Sequence

The purified GDH derived from NBRC6231 was dissolved in Tris-HCl buffer (pH 6.8) containing 0.1% SDS and 10% glycerol, and partially digested by adding Glu specific V8 endoprotease at a final concentration of 10 μg/mL thereto and incubating at 37° C. for 16 hours. This sample was electrophoresed on 16% acrylamide gel to separate peptides. Peptide molecules present in this gel were transferred on a PVDF membrane using the buffer for blotting (1.4% glycine, 0.3% Tris and 20% ethanol) by semi-dry method. The peptides transferred onto the PVDF membrane were stained using a CBB staining kit (GelCode Blue Stain Reagent supplied from PIERCE), two band portions of the visualized peptide fragments were cut out and internal amino acid sequences were analyzed using a peptide sequencer. The resulting amino acid sequences were IGGVVDTSLKVYGT (SEQ ID NO:9) and WGGGTKQTVRAGKALGGTST (SEQ ID NO: 10). Based on this sequence, degenerate primers containing mixed bases were made, and PCR was performed using the cDNA derived from NBRC6231 as the template. An amplified product was obtained, and was detected as a single band of about 1.4 kb by agarose gel electrophoresis. This band was cut out, and extracted and purified using MagExtractor-PCR&Gel Clean Up supplied from Toyobo Co., Ltd. The purified DNA fragment was TA-cloned using TArget Clone-Plus, and *Escherichia coli* JM 109 competent cells (Competent High JM109 supplied from Toyobo Co., Ltd.) were transformed with the resulting vector by heat shock. Among transformed clones, for colonies in which an insert had been identified by blue-white determination, the plasmid was extracted and purified using MagExtractor-Plasmid by miniprep, and the base sequence (1356 bp) of the insert was determined using plasmid sequence specific primers.

[5] Estimation of AOGDH Gene

Based on the determined base sequence, the homology was searched on the home page of "NCBI BLAST," and the AOGDH gene was estimated from multiple candidate sequences in consideration of the homology to publicly known glucose oxidation enzymes. The homology of the AOGDH estimated from the search to the GDH partial sequence derived from *P. lilacinoechinulatum* NBRC6231 was 49% at an amino acid level.

Example 2

Acquisition of AOGDH Gene and Introduction into *Escherichia coli*

For obtaining the AOGDH gene, mRNA was prepared from the microbial cells of *Aspergillus oryzae* TI strain, and cDNA was synthesized. Two oligo DNA represented by SEQ ID NOS:6 and 7 were synthesized, and the AOGDH gene was amplified using the prepared cDNA as the template and using KOD Plus DNA polymerase (supplied from Toyobo Co., Ltd.). A recombinant plasmid was constructed by treating the resulting DNA fragment with Nde I and Bam H I and inserting it into Nde I-Bam H I sites in pBluescript (the Nde I site had been introduced to match a Nde I recognition sequence ATG to a translation initiation codon ATG of LacZ). *Escherichia coli* DH5α (supplied from Toyobo Co., Ltd.) was transformed with this recombinant plasmid. The plasmid was extracted from the transformant according to the standard method, and the base sequence of the AOGDH gene was determined (SEQ ID NO:5). As a result, it was found that the amino acid sequence deduced from the cDNA sequence was composed of 593 amino acid residues (SEQ ID NO:4). GDH predicted from RIB40 strain registered in the database is composed of 588 amino acid residues (SEQ ID NO:3), suggesting that the GDH from RIB40 strain and the GDH from TI strain are different in amino acid residue number. For the gene, the sequence was identified using TI strain genomic DNA, and the gene flanking regions were identified using RACE method. It was suggested that RIB40 strain which was the database strain and TI strain were different in GDH gene sequence. Thus, using the recombinant plasmid containing TI strain GDH gene as the template, the recombinant plasmid containing the GDH gene sequence predicted from the sequence of the database RIB40 strain was made using QuickChange Site Directed Mutagenesis Kit (supplied from Stratagene), and the transformant was acquired. These transformants were cultured with shaking in a liquid medium (Terrific broth) containing 100 μg/mL of ampicillin at 30° C. for 16 hours. When the GDH activity was measured in disrupted microbial cell solutions, no GDH activity could be identified in the transformant having the GDH sequence derived from RIB40 strain whereas the high GDH activity of 8.0 U per mL of the culture medium was obtained in the transformant having the GDH sequence derived from TI strain. The GDH activity in the culture supernatant of *Aspergillus oryzae* TI strain in Example 1 was 0.2 U/mL. These results suggested that the GDH gene predicted from the RIB40 database sequence did not function as GDH. So far as the gene sequences of TI strain and RIB40 strain were compared, it was thought that the partial deletion in the GDH gene sequence derived from RIB40 strain caused it.

Example 3

The *Escherichia coli* DH5α transformant having the GDH sequence derived from TI strain cultured in Example 2 was collected by centrifugation, the microbial cells were suspended in 20 mM potassium phosphate buffer (pH 6.5), and then disrupted using French press to extract GDH. This was treated by the same procedure as in AOGDH purified in Example 1 to yield a purified enzyme preparation (rAOGDH). Its properties were compared with those of the AOGDH purified enzyme preparation.

[1] Substrate Specificity

When the blood glucose level is measured using a blood glucose sensor, it is required to use the enzyme specific for glucose not to lead to misdiagnosis. Thus, the reactivity of rAOGDH to various sugars was examined. The results are shown in Table 1. It was confirmed that rAOGDH and AOGDH exhibited the equivalent substrate specificity and did not act upon maltose to which reactivity was particularly problematic when the patient using transfusion used the sensor.

TABLE 1

|  | *Aspergillus oryzae* AOGDH | Recombinant rAOGDH |
| --- | --- | --- |
| Glucose | 100.0 | 100.0 |
| Maltose | 0.4 | 0 |
| Fructose | 0 | 0.2 |
| Arabinose | 0 | 0.3 |
| Glycerin | 0.1 | 0.2 |
| Sucrose | 0.1 | 0 |
| Melezitose | 0 | 0.5 |
| Sorbose | 0 | 0 |
| Ribose | 0 | 0.1 |
| Maltotriose | 0.2 | 0.2 |
| Maltotetraose | 0.7 | 0.2 |
| Galactose | 0.4 | 0.6 |
| Mannose | 0.8 | 2.1 |
| Trehalose | 0.5 | 1.0 |

[2] Maltose Degradability

Even if GDH itself used for the blood glucose sensor does not act upon maltose, when the component to degrade maltose into glucose is contained in the enzyme preparation, it potentially leads to the misdiagnosis. That is, it is extremely important that the component to degrade maltose is not contained in the GDH enzyme preparation. Thus, the contamination of the component to degrade maltose in the GDH enzyme preparation was examined. A test for the contamination of the component to degrade maltose was performed as follows. Maltose (8 mM, 50 μL) was added to 50 μL of each purified enzyme solution prepared at 10 U/mL, and reacted at 37° C. After the completion of the reaction, the concentration of glucose contained in the reaction solution was examined using Liquitec glucose HK test (supplied from Roche Diagnostics). A standard curve for calculating the glucose concentration was made by measuring glucose solutions for setting a standard coefficient (supplied from Wako Pure Chemical Industries Inc.). The results are shown in Table 2.

TABLE 2

|  |  | Reaction time | | | |
| --- | --- | --- | --- | --- | --- |
|  | Purified enzyme | 30 sec | 60 sec | 3 min | 10 min |
| Free glucose concentration (mM) | AOGDH | 7.10 | 7.15 | 7.37 | 7.89 |
|  | rAOGDH (recombinant) | 0 | 0.030 | 0.005 | 0 |
| Maltose degradation ratio | AOGDH | 89% | 89% | 92% | 99% |
|  | rAOGDH (recombinant) | 0% | 0.38% | 0.06% | 0% |

In the AOGDH purified preparation, after treating at 37° C. for 30 seconds, 90% of maltose was already degraded into glucose, and after reacting for 10 minutes, nearly 100% maltose was degraded. Thus, the same measurement was performed using the preparation obtained by highly purifying AOGDH for the purpose of the analysis of the partial amino acid sequence in Example 1, but the activity to degrade maltose was identified. Meanwhile, in the rAOGDH preparation, even after treating at 37° C. for 10 minutes, the accumulation of glucose was not observed at all. *Aspergillus oryzae* has been utilized for fermentation industry from a long time ago, and has been known to produce sugar-related enzymes such as amylase and glucoamylase in large amounts. Thus, it is thought that it is extremely difficult to purify only GDH at high purity under such an environment.

From these results, it is thought that it is essential to use GDH prepared from the recombinant gene when GDH derived from *Aspergillus oryzae* is used for the blood glucose sensor.

INDUSTRIAL APPLICABILITY

The present invention enables to produce glucose dehydrogenase derived from *Aspergillus oryzae* on a large scale by the use of recombinant *Escherichia coli*. By the present invention, it becomes possible to produce glucose dehydrogenase which does not act upon maltose in a broad sense and is suitable for the glucose sensor and the like.

The invention claimed is:

1. An isolated protein comprising the amino acid sequence of SEQ ID NO: 4.

2. An isolated protein consisting of the protein of claim 1.

3. A glucose sensor comprising the protein of claim 1.

4. A glucose sensor comprising the protein of claim 2.

* * * * *

SEQUENCE LISTING

<160> NUMBER OF SEQ ID NOS: 10

<210> SEQ ID NO 1
<211> LENGTH: 1923
<212> TYPE: DNA
<213> ORGANISM: Aspergillus oryzae

<400> SEQUENCE: 1

```
atgctcttct cactggcatt cctgagtgcc ctgtcgctgg ccacggcatc accggctgga       60
cgggccaaga acactacgac atacgactac atcgttgtgg gaggcggcac aagtggtctt      120
gtggtcgcaa atcgcctttc tgagaacccc gatgtctccg ttcttctgct tgaggccggt      180
gcttctgtgt tcaacaaccc ggacgtaacc aacgctaacg gttatggatt ggcctttggc      240
tcggccatcg actggcagta ccagtctatt aaccaaagct atgcaggagg taaacagcaa      300
gttctgcgtg ctggtaaggc ccttggagga accagtacaa tcaatggtat gcttctatgg      360
atgatctctt agtcggcatg gaccactgac gaccacagga atggcctata cccgcgcaga      420
ggatgtccag attgacgttt ggcagaaact tggaaacgaa ggttggacgt ggaaagatct      480
cctaccatac tacctgaaga gtgaaaactt gacggcccct accagctctc aggttgctgc      540
tggcgctgct tataaccctg ccgtgaatgg aaaagaaggt cctctcaagg tcggctggtc      600
gggaagcctg gcctccggta atctgtcagt tgctctgaac cgtacgttcc aagccatgga      660
ggatgtcaat ggaggcaaga tgcgtggctt caacatctac ccatccaccc tcgacgttga      720
cctcaatgtc cgcgaagatg cagcccgggc atactacttc ccttatgatg acaggaagaa      780
ccttcacctg ctggagaaca ccactgccaa ccgccttttc tggaagaacg gctctgctga      840
ggaagctatt gcggatggtg tcgagatcac ctccgctgat ggcaaggtca ctcgtgtgca      900
tgcaaagaaa gaggtcatca tctctgctgg tgccctgcgg tctcctctca ttctcgagct      960
ttcaggagtt ggaaacccaa cgtaagtgtt ccactgatgc cagcccctct ctatcaccgt     1020
ctctgaccct cgtagcatcc tcaaaaagaa caacataacc ccacgtgtcg atctccccac     1080
cgttggggag aacctccaag accagttcaa caacggcatg gctggcgaag atacggcgt     1140 ccttgccggt gcctcaaccg tgacctaccc ttccatctcc gacgtcttcg gtaacgagac     1200
tgactctatc gttgcatctc tccgatctca actctccgac tacgccgccg cgaccgtcaa     1260
ggtcagcaac ggccacatga agcaggagga ccttgagcgc ctctaccagc tccaatttga     1320
cctcatcgtc aaggacaagg tccctatcgc cgagatcctc ttccaccccg gtggtggaaa     1380
cgccgtgtcc tccgaattct ggggcttgct tccccttcgcc cgtggcaaca tccacattag     1440
ctccaatgac ccgactgctc ccgccgccat caaccctaac tactttatgt tcgaatggga     1500
```

```
cggcaagagc caggccggta tcgccaagta catcaggaag attctccgca gcgcaccatt   1560
gaacaaactt attgcgaagg aaaccaagcc cggtctctct gagattccgg ccactgctgc   1620
ggatgagaag tgggttgaat ggctcaaggc taactgtaag ttgaatcctt tcttggcttc   1680
gatggtgagt ctgacgtgag ctctctagat cgttccaact tccacccccgt cggaactgct   1740 gccatgatgc ctcgttccat tggtggcgtt gttgataacc gtctccgggt ctatggtacc   1800
agcaatgttc gcgtcgtaga tgcgtctgtc ctgcccttcc aggtttgcgg ccacttggtt   1860
agcacgcttt atgccgttgc cgagcgcgct tccgacttga ttaaggagga tgcgaagagt   1920
gct                                                                 1923

<210> SEQ ID NO 2
<211> LENGTH: 1767
<212> TYPE: DNA
<213> ORGANISM: Aspergillus oryzae

<400> SEQUENCE: 2
atgctcttct cactggcatt cctgagtgcc ctgtcgctgg ccacggcatc accggctgga     60
cgggccaaga acactacgac atacgactac atcgttgtgg gaggcggcac aagtggtctt    120
gtggtcgcaa atcgcctttc tgagaacccc gatgtctccg ttcttctgct tgaggccggt    180
gcttctgtgt caacaacccc ggacgtaacc aacgctaacg ttatggatt ggcctttggc     240 tcggccatcg actggcagta ccagtctatt aaccaaagct atgcaggagg taaacagcaa    300
gttctgcgtg ctggtaaggc ccttggagga accagtacaa tcaatggaat ggcctatacc    360
cgcgcagagg atgtccagat tgacgtttgg cagaaacttg aaacgaaagg ttggacgtgg    420
aaagatctcc taccatacta cctgaagagt gaaaacttga cggcccctac cagctctcag    480
gttgctgctg gcgctgctta taaccctgcc gtgaatggaa agaaggtcc tctcaaggtc     540 ggctggtcgg gaagcctggc ctccggtaat ctgtcagttg ctctgaaccg tacgttccaa    600
gccatggagg atgtcaatgg aggcaagatg cgtggcttca acatctaccc atccacccct    660
gacgttgacc tcaatgtccg cgaagatgca gcccgggcat actacttccc ttatgatgac    720
aggaagaacc ttcacctgct ggagaacacc actgccaacc gccttttctg gaagaacggc    780
tctgctgagg aagctattgc ggatggtgtc gagatcacct ccgctgatgg caaggtcact    840
cgtgtgcatg caaagaaaga ggtcatcatc tctgctggtg ccctgcggtc tcctctcatt    900
ctcgagcttt caggagttgg aaacccaacc atcctcaaaa agaacaacat aaccccacgt    960
gtcgatctcc ccaccgttgg ggagaacctc caagaccagt caacaacgg catggctggc    1020 gaaggatacg gcgtccttgc cggtgcctca accgtgacct acccttccat ctccgacgtc   1080
ttcggtaacg agactgactc tatcgttgca tctctccgat ctcaactctc cgactacgcc   1140
gccgcgaccg tcaaggtcag caacggccac atgaagcagg aggaccttga gcgcctctac   1200
cagctccaat ttgacctcat cgtcaaggac aaggtcccta tcgccgagat cctcttccac   1260
cccggtggtg aaacgccgt gtcctccgaa ttctggggct tgcttcccctt cgcccgtggc   1320 aacatccaca ttagctccaa tgacccgact gctcccgccg ccatcaaccc taactacttt   1380
atgttcgaat gggacggcaa gagccaggcc ggtatcgcca agtacatcag gaagattctc   1440
cgcagcgcac cattgaacaa acttattgcg aaggaaaacca agcccggtct ctctgagatt   1500
ccggccactg ctgcggatga gaagtgggtt gaatggctca aggctaacta tcgttccaac   1560 ttccacccccg tcggaactgc tgccatgatg cctcgttcca ttggtggcgt tgttgataac   1620
cgtctccggg tctatggtac cagcaatgtt cgcgtcgtag atgcgtctgt cctgcccttc   1680
```

-continued

```
caggtttgcg gccacttggt tagcacgctt tatgccgttg ccgagcgcgc ttccgacttg    1740
attaaggagg atgcgaagag tgcttag                                        1767
```

<210> SEQ ID NO 3
<211> LENGTH: 588
<212> TYPE: PRT
<213> ORGANISM: Aspergillus oryzae

<400> SEQUENCE: 3

| | | | | | | | | | | | | | | |
|---|---|---|---|---|---|---|---|---|---|---|---|---|---|---|
| Met | Leu | Phe | Ser | Leu | Ala | Phe | Leu | Ser | Ala | Leu | Ser | Leu | Ala | Thr | Ala |
| 1 | | | | 5 | | | | | 10 | | | | | 15 | |
| Ser | Pro | Ala | Gly | Arg | Ala | Lys | Asn | Thr | Thr | Tyr | Asp | Tyr | Ile | Val | |
| | | | 20 | | | | | 25 | | | | | 30 | | |
| Val | Gly | Gly | Gly | Thr | Ser | Gly | Leu | Val | Val | Ala | Asn | Arg | Leu | Ser | Glu |
| | | 35 | | | | | 40 | | | | | 45 | | | |
| Asn | Pro | Asp | Val | Ser | Val | Leu | Leu | Leu | Glu | Ala | Gly | Ala | Ser | Val | Phe |
| | 50 | | | | | 55 | | | | | 60 | | | | |
| Asn | Asn | Pro | Asp | Val | Thr | Asn | Ala | Asn | Gly | Tyr | Gly | Leu | Ala | Phe | Gly |
| 65 | | | | | 70 | | | | | 75 | | | | | 80 |
| Ser | Ala | Ile | Asp | Trp | Gln | Tyr | Gln | Ser | Ile | Asn | Gln | Ser | Tyr | Ala | Gly |
| | | | | 85 | | | | | 90 | | | | | 95 | |
| Gly | Lys | Gln | Gln | Val | Leu | Arg | Ala | Gly | Lys | Ala | Leu | Gly | Gly | Thr | Ser |
| | | | 100 | | | | | 105 | | | | | 110 | | |
| Thr | Ile | Asn | Gly | Met | Ala | Tyr | Thr | Arg | Ala | Glu | Asp | Val | Gln | Ile | Asp |
| | | 115 | | | | | 120 | | | | | 125 | | | |
| Val | Trp | Gln | Lys | Leu | Gly | Asn | Glu | Gly | Trp | Thr | Trp | Lys | Asp | Leu | Leu |
| 130 | | | | | 135 | | | | | 140 | | | | | |
| Pro | Tyr | Tyr | Leu | Lys | Ser | Glu | Asn | Leu | Thr | Ala | Pro | Thr | Ser | Ser | Gln |
| 145 | | | | | 150 | | | | | 155 | | | | | 160 |
| Val | Ala | Ala | Gly | Ala | Ala | Tyr | Asn | Pro | Ala | Val | Asn | Gly | Lys | Glu | Gly |
| | | | | 165 | | | | | 170 | | | | | 175 | |
| Pro | Leu | Lys | Val | Gly | Trp | Ser | Gly | Ser | Leu | Ala | Ser | Gly | Asn | Leu | Ser |
| | | | 180 | | | | | 185 | | | | | 190 | | |
| Val | Ala | Leu | Asn | Arg | Thr | Phe | Gln | Ala | Met | Glu | Asp | Val | Asn | Gly | Gly |
| | | 195 | | | | | 200 | | | | | 205 | | | |
| Lys | Met | Arg | Gly | Phe | Asn | Ile | Tyr | Pro | Ser | Thr | Leu | Asp | Val | Asp | Leu |
| 210 | | | | | 215 | | | | | 220 | | | | | |
| Asn | Val | Arg | Glu | Asp | Ala | Ala | Arg | Ala | Tyr | Tyr | Phe | Pro | Tyr | Asp | Asp |
| 225 | | | | | 230 | | | | | 235 | | | | | 240 |
| Arg | Lys | Asn | Leu | His | Leu | Leu | Glu | Asn | Thr | Thr | Ala | Asn | Arg | Leu | Phe |
| | | | | 245 | | | | | 250 | | | | | 255 | |
| Trp | Lys | Asn | Gly | Ser | Ala | Glu | Glu | Ala | Ile | Ala | Asp | Gly | Val | Glu | Ile |
| | | | 260 | | | | | 265 | | | | | 270 | | |
| Thr | Ser | Ala | Asp | Gly | Lys | Val | Thr | Arg | Val | His | Ala | Lys | Lys | Glu | Val |
| | | 275 | | | | | 280 | | | | | 285 | | | |
| Ile | Ile | Ser | Ala | Gly | Ala | Leu | Arg | Ser | Pro | Leu | Ile | Leu | Glu | Leu | Ser |
| 290 | | | | | 295 | | | | | 300 | | | | | |
| Gly | Val | Gly | Asn | Pro | Thr | Ile | Leu | Lys | Lys | Asn | Asn | Ile | Thr | Pro | Arg |
| 305 | | | | | 310 | | | | | 315 | | | | | 320 |
| Val | Asp | Leu | Pro | Thr | Val | Gly | Glu | Asn | Leu | Gln | Asp | Gln | Phe | Asn | Asn |
| | | | | 325 | | | | | 330 | | | | | 335 | |
| Gly | Met | Ala | Gly | Glu | Gly | Tyr | Gly | Val | Leu | Ala | Gly | Ala | Ser | Thr | Val |
| | | | 340 | | | | | 345 | | | | | 350 | | |

```
Thr Tyr Pro Ser Ile Ser Asp Val Phe Gly Asn Glu Thr Asp Ser Ile
        355                 360                 365

Val Ala Ser Leu Arg Ser Gln Leu Ser Asp Tyr Ala Ala Ala Thr Val
    370                 375                 380

Lys Val Ser Asn Gly His Met Lys Gln Glu Asp Leu Glu Arg Leu Tyr
385                 390                 395                 400

Gln Leu Gln Phe Asp Leu Ile Val Lys Asp Lys Val Pro Ile Ala Glu
            405                 410                 415

Ile Leu Phe His Pro Gly Gly Asn Ala Val Ser Ser Glu Phe Trp
            420                 425                 430

Gly Leu Leu Pro Phe Ala Arg Gly Asn Ile His Ile Ser Ser Asn Asp
        435                 440                 445

Pro Thr Ala Pro Ala Ala Ile Asn Pro Asn Tyr Phe Met Phe Glu Trp
    450                 455                 460

Asp Gly Lys Ser Gln Ala Gly Ile Ala Lys Tyr Ile Arg Lys Ile Leu
465                 470                 475                 480

Arg Ser Ala Pro Leu Asn Lys Leu Ile Ala Lys Glu Thr Lys Pro Gly
            485                 490                 495

Leu Ser Glu Ile Pro Ala Thr Ala Ala Asp Glu Lys Trp Val Glu Trp
            500                 505                 510

Leu Lys Ala Asn Tyr Arg Ser Asn Phe His Pro Val Gly Thr Ala Ala
        515                 520                 525

Met Met Pro Arg Ser Ile Gly Gly Val Val Asp Asn Arg Leu Arg Val
    530                 535                 540

Tyr Gly Thr Ser Asn Val Arg Val Val Asp Ala Ser Val Leu Pro Phe
545                 550                 555                 560

Gln Val Cys Gly His Leu Val Ser Thr Leu Tyr Ala Val Ala Glu Arg
            565                 570                 575

Ala Ser Asp Leu Ile Lys Glu Asp Ala Lys Ser Ala
        580                 585

<210> SEQ ID NO 4
<211> LENGTH: 593
<212> TYPE: PRT
<213> ORGANISM: Aspergillus oryzae

<400> SEQUENCE: 4

Met Leu Phe Ser Leu Ala Phe Leu Ser Ala Leu Ser Leu Ala Thr Ala
1               5                   10                  15

Ser Pro Ala Gly Arg Ala Lys Asn Thr Thr Tyr Asp Tyr Ile Val
            20                  25                  30

Val Gly Gly Gly Thr Ser Gly Leu Val Val Ala Asn Arg Leu Ser Glu
        35                  40                  45

Asn Pro Asp Val Ser Val Leu Leu Glu Gly Ala Ser Val Phe
    50                  55                  60

Asn Asn Pro Asp Val Thr Asn Ala Asn Gly Tyr Gly Leu Ala Phe Gly
65                  70                  75                  80

Ser Ala Ile Asp Trp Gln Tyr Gln Ser Ile Asn Gln Ser Tyr Ala Gly
            85                  90                  95

Gly Lys Gln Gln Val Leu Arg Ala Gly Lys Ala Leu Gly Gly Thr Ser
        100                 105                 110

Thr Ile Asn Gly Met Ala Tyr Thr Arg Ala Glu Asp Val Gln Ile Asp
    115                 120                 125

Val Trp Gln Lys Leu Gly Asn Glu Gly Trp Thr Trp Lys Asp Leu Leu
    130                 135                 140
```

```
Pro Tyr Tyr Leu Lys Ser Glu Asn Leu Thr Ala Pro Thr Ser Ser Gln
145                 150                 155                 160

Val Ala Ala Gly Ala Ala Tyr Asn Pro Ala Val Asn Gly Lys Glu Gly
            165                 170                 175

Pro Leu Lys Val Gly Trp Ser Gly Ser Leu Ala Ser Gly Asn Leu Ser
            180                 185                 190

Val Ala Leu Asn Arg Thr Phe Gln Ala Ala Gly Val Pro Trp Val Glu
            195                 200                 205

Asp Val Asn Gly Gly Lys Met Arg Gly Phe Asn Ile Tyr Pro Ser Thr
            210                 215                 220

Leu Asp Val Asp Leu Asn Val Arg Glu Asp Ala Ala Arg Ala Tyr Tyr
225                 230                 235                 240

Phe Pro Tyr Asp Asp Arg Lys Asn Leu His Leu Leu Glu Asn Thr Thr
            245                 250                 255

Ala Asn Arg Leu Phe Trp Lys Asn Gly Ser Ala Glu Glu Ala Ile Ala
            260                 265                 270

Asp Gly Val Glu Ile Thr Ser Ala Asp Gly Lys Val Thr Arg Val His
            275                 280                 285

Ala Lys Lys Glu Val Ile Ile Ser Ala Gly Ala Leu Arg Ser Pro Leu
            290                 295                 300

Ile Leu Glu Leu Ser Gly Val Gly Asn Pro Thr Ile Leu Lys Lys Asn
305                 310                 315                 320

Asn Ile Thr Pro Arg Val Asp Leu Pro Thr Val Gly Glu Asn Leu Gln
            325                 330                 335

Asp Gln Phe Asn Asn Gly Met Ala Gly Glu Gly Tyr Gly Val Leu Ala
            340                 345                 350

Gly Ala Ser Thr Val Thr Tyr Pro Ser Ile Ser Asp Val Phe Gly Asn
            355                 360                 365

Glu Thr Asp Ser Ile Val Ala Ser Leu Arg Ser Gln Leu Ser Asp Tyr
            370                 375                 380

Ala Ala Ala Thr Val Lys Val Ser Asn Gly His Met Lys Gln Glu Asp
385                 390                 395                 400

Leu Glu Arg Leu Tyr Gln Leu Gln Phe Asp Leu Ile Val Lys Asp Lys
            405                 410                 415

Val Pro Ile Ala Glu Ile Leu Phe His Pro Gly Gly Gly Asn Ala Val
            420                 425                 430

Ser Ser Glu Phe Trp Gly Leu Leu Pro Phe Ala Arg Gly Asn Ile His
            435                 440                 445

Ile Ser Ser Asn Asp Pro Thr Ala Pro Ala Ala Ile Asn Pro Asn Tyr
450                 455                 460

Phe Met Phe Glu Trp Asp Gly Lys Ser Gln Ala Gly Ile Ala Lys Tyr
465                 470                 475                 480

Ile Arg Lys Ile Leu Arg Ser Ala Pro Leu Asn Lys Leu Ile Ala Lys
            485                 490                 495

Glu Thr Lys Pro Gly Leu Ser Glu Ile Pro Ala Thr Ala Ala Asp Glu
            500                 505                 510

Lys Trp Val Glu Trp Leu Lys Ala Asn Tyr Arg Ser Asn Phe His Pro
            515                 520                 525

Val Gly Thr Ala Ala Met Met Pro Arg Ser Ile Gly Gly Val Val Asp
            530                 535                 540

Asn Arg Leu Arg Val Tyr Gly Thr Ser Asn Val Arg Val Val Asp Ala
545                 550                 555                 560
```

-continued

Ser Val Leu Pro Phe Gln Val Cys Gly His Leu Val Ser Thr Leu Tyr
              565                 570                 575

Ala Val Ala Glu Arg Ala Ser Asp Leu Ile Lys Glu Asp Ala Lys Ser
          580                 585                 590

Ala

<210> SEQ ID NO 5
<211> LENGTH: 1779
<212> TYPE: DNA
<213> ORGANISM: Aspergillus oryzae

<400> SEQUENCE: 5

| | | | | | |
|---|---|---|---|---|---|
| atgctcttct | cactggcatt | cctgagtgcc | ctgtcgctgg | ccacggcatc | accggctgga | 60 |
| cgggccaaga | acactacgac | atacgactac | atcgttgtgg | gaggcggcac | aagtggtctt | 120 |
| gtggtcgcaa | atcgcctttc | tgagaacccc | gatgtctccg | ttcttctgct | tgaggccggt | 180 |
| gcttctgtgt | caacaacccc | ggacgtaacc | aacgctaacg | gttatggatt | ggcctttggc | 240 |
| tcggccatcg | actggcagta | ccagtctatt | aaccaaagct | atgcaggagg | taaacagcaa | 300 |
| gttctgcgtg | ctggtaaggc | ccttggagga | accagtacaa | tcaatggaat | ggcctatacc | 360 |
| cgcgcagagg | atgtccagat | tgacgtttgg | cagaaacttg | aaacgaaggg | ttggacgtgg | 420 |
| aaagatctcc | tactactacta | cctgaagagt | gaaaacttga | cggcccctac | cagctctcag | 480 |
| gttgctgctg | cgctgctta | taaccctgcc | gtgaatggaa | agaaggtcc | tctcaaggtc | 540 |
| ggctggtcgg | gaagcctggc | ctccggtaat | ctgtcagttg | ctctgaaccg | tacgttccaa | 600 |
| gccgctggtg | ttccatgggt | tgaggatgtc | aatggaggca | agatgcgtgg | cttcaacatc | 660 |
| tacccatcca | ccctcgacgt | tgacctcaat | gtccgcgaag | atgcagcccg | ggcatactac | 720 |
| ttcccttatg | atgacaggaa | gaaccttcac | ctgctggaga | acaccactgc | caaccgcctt | 780 |
| ttctggaaga | acggctctgc | tgaggaagct | attgcggatg | tgtcgagat | cacctccgct | 840 |
| gatggcaagg | tcactcgtgt | gcatgcaaag | aaagaggtca | tcatctctgc | tggtgccctg | 900 |
| cggtctcctc | tcattctcga | gctttcagga | gttggaaacc | caaccatcct | caaaaagaac | 960 |
| aacataaccc | cacgtgtcga | tctccccacc | gttggggaga | acctccaaga | ccagttcaac | 1020 |
| aacggcatgg | ctggcgaagg | atacggcgtc | cttgccggtg | cctcaaccgt | gacctaccct | 1080 |
| tccatctccg | acgtcttcgg | taacgagact | gactctatcg | ttgcatctct | ccgatctcaa | 1140 |
| ctctccgact | acgccgccgc | gaccgtcaag | gtcagcaacg | ccacatgaa | gcaggaggac | 1200 |
| cttgagcgcc | tctaccagct | ccaatttgac | ctcatcgtca | aggacaaggt | ccctatcgcc | 1260 |
| gagatcctct | tccaccccgg | tgtggaaaac | gccgtgtcct | ccgaattctg | gggcttgctt | 1320 |
| cccttcgccc | gtggcaacat | ccacattagc | tccaatgacc | cgactgctcc | cgccgccatc | 1380 |
| aaccctaact | actttatgtt | cgaatgggac | ggcaagagcc | aggccggtat | cgccaagtac | 1440 |
| atcaggaaga | ttctccgcag | cgcaccattg | aacaaactta | ttgcgaagga | aaccaagccc | 1500 |
| ggtctctctg | agattccggc | cactgctgcg | gatgagaagt | gggttgaatg | gctcaaggct | 1560 |
| aactatcgtt | ccaacttcca | ccccgtcgga | actgctgcca | tgatgcctcg | ttccattggt | 1620 |
| ggcgttgttg | ataaccgtct | ccgggtctat | ggtaccagca | atgttcgcgt | cgtagatgcg | 1680 |
| tctgtcctgc | ccttccaggt | tgcggccac | ttggttagca | cgctttatgc | cgttgccgag | 1740 |
| cgcgcttccg | acttgattaa | ggaggatgcg | aagagtgct | | | 1779 |

<210> SEQ ID NO 6
<211> LENGTH: 34

```
<212> TYPE: DNA
<213> ORGANISM: Artificial Sequence
<220> FEATURE:
<223> OTHER INFORMATION: The sequence of designed polynucleotide
      described in Example 1

<400> SEQUENCE: 6
ggaattccat atgctcttct cactggcatt cctg                                    34

<210> SEQ ID NO 7
<211> LENGTH: 35
<212> TYPE: DNA
<213> ORGANISM: Artificial Sequence
<220> FEATURE:
<223> OTHER INFORMATION: The sequence of designed polynucleotide
      described in Example 1

<400> SEQUENCE: 7
cgggatccga attggtacgg gacactgtcc ctacg                                   35

<210> SEQ ID NO 8
<211> LENGTH: 1938
<212> TYPE: DNA
<213> ORGANISM: Aspergillus oryzae

<400> SEQUENCE: 8
atgctcttct cactggcatt cctgagtgcc ctgtcgctgg ccacggcatc accggctgga        60
cgggccaaga acactacgac atacgactac atcgttgtgg gaggcggcac aagtggtctt       120
gtggtcgcaa atcgcctttc tgagaacccc gatgtctccg ttcttctgct tgaggccggt       180
gcttctgtgt caacaaccc ggacgtaacc aacgctaacg ttatggatt ggcctttggc        240 tcggccatcg actggcagta ccagtctatt aaccaaagct atgcaggagg taaacagcaa       300
gttctgcgtg ctggtaaggc ccttggagga accagtacaa tcaatggtat gcttctatgg       360
atgatctctt agtcggcatg gaccactgac gaccacagga atggcctata cccgcgcaga       420
ggatgtccag attgacgttt ggcagaaact tggaaacgaa ggttggacgt ggaaagatct       480
cctaccatac tacctgaaga gtgaaaactt gacggcccct accagctctc aggttgctgc       540
tggcgctgct tataaccctg ccgtgaatgg aaaagaaggt cctctcaagg tcggctggtc       600
gggaagcctg gcctccggta atctgtcagt tgctctgaac cgtacgttcc aagccgctgg       660
tgttccatgg gttgaggatg tcaatggagg caagatgcgt ggcttcaaca tctacccatc       720
caccctcgac gttgacctca atgtccgcga agatgcagcc cggcatact acttcctta        780 tgatgacagg aagaaccttc acctgctgga gaacaccact gccaaccgcc ttttctggaa       840
gaacggctct gctgaggaag ctattgcgga tggtgtcgag atcacctccg ctgatggcaa       900
ggtcactcgt gtgcatgcaa agaaagaggt catcatctct gctggtgccc tgcggtctcc       960
tctcattctc gagctttcag gagttggaaa cccaacgtaa gtgttccact gatgccagcc      1020
cctctctatc accgtctctg accctcgtag catcctcaaa aagaacaaca taccccacg       1080 tgtcgatctc cccaccgttg gggagaacct ccaagaccag ttcaacaacg gcatggctgg      1140
cgaaggatac ggcgtccttg ccggtgcctc aacgtgacc taccttcca tctccgacgt       1200 cttcggtaac gagactgact ctatcgttgc atctctccga tctcaactct ccgactacgc      1260
cgccgcgacc gtcaaggtca gcaacggcca catgaagcag gaggaccttg agcgcctcta      1320
ccagctccaa tttgacctca tcgtcaagga caaggtccct atcgccgaga tcctcttcca      1380
ccccggtggt ggaaacgccg tgtcctccga attctggggc ttgcttccct tcgccgtgg       1440
```

-continued

```
caacatccac attagctcca atgacccgac tgctcccgcc gccatcaacc ctaactactt    1500
tatgttcgaa tgggacggca agagccaggc cggtatcgcc aagtacatca ggaagattct    1560
ccgcagcgca ccattgaaca aacttattgc gaaggaaacc aagcccggtc tctctgagat    1620
tccggccact gctgcggatg agaagtgggt tgaatggctc aaggctaact gtaagttgaa    1680
tcctttcttg gcttcgatgg tgagtctgac gtgagctctc tagatcgttc caacttccac    1740
cccgtcggaa ctgctgccat gatgcctcgt tccattggtg gcgttgttga taaccgtctc    1800
cgggtctatg gtaccagcaa tgttcgcgtc gtagatgcgt ctgtcctgcc cttccaggtt    1860
tgcggccact tggttagcac gctttatgcc gttgccgagc gcgcttccga cttgattaag    1920
gaggatgcga agagtgct                                                  1938
```

```
<210> SEQ ID NO 9
<211> LENGTH: 14
<212> TYPE: PRT
<213> ORGANISM: Artificial Sequence
<220> FEATURE:
<223> OTHER INFORMATION: The sequence of peptide fragment
      described in example 1

<400> SEQUENCE: 9

Ile Gly Gly Val Val Asp Thr Ser Leu Lys Val Tyr Gly Thr
1               5                   10

<210> SEQ ID NO 10
<211> LENGTH: 20
<212> TYPE: PRT
<213> ORGANISM: Artificial Sequence
<220> FEATURE:
<223> OTHER INFORMATION: The sequence of peptide fragment
      described in example 1

<400> SEQUENCE: 10

Trp Gly Gly Gly Thr Lys Gln Thr Val Arg Ala Gly Lys Ala Leu Gly
1               5                   10                  15

Gly Thr Ser Thr
            20
```